United States Patent [19]

Shaku et al.

[11] Patent Number: 5,468,475
[45] Date of Patent: Nov. 21, 1995

[54] COSMETIC COMPOSITION WITH CHOLINE DERIVATIVE

[75] Inventors: Masao Shaku; Sayuri Ohkura; Hideo Kuroda; Ai Kano, all of Yokohama; Nobuo Nakabayashi, 5-6-20, Koganehara, Matsudo-shi, Chiba-ken, all of Japan

[73] Assignees: Pola Chemical Industries Inc.; Nobuo Nakabayashi

[21] Appl. No.: 153,414

[22] Filed: Nov. 15, 1993

[30] Foreign Application Priority Data

Nov. 17, 1992 [JP] Japan .................................. 4-306751

[51] Int. Cl.⁶ .......................... A61K 7/06; A61K 31/78; A61K 31/66
[52] U.S. Cl. ..................... 424/70.16; 424/78.03
[58] Field of Search ................. 424/401, 63, 64, 424/69, 70.1, 70.16, 401, 78.03

[56] References Cited

PUBLICATIONS

CA 119:56226w 1993 N. Nakabayashi et al.
CA 116:24680 1991 K. Ishihara et al.
CA 118:154413 1991 K. Ishihara et al.
C.A. 119:34118 Shaku et al. 1993
Patent Abstracts of Japan, vol. 3, No. 87 (C-053) JPA-54-63,025; May 21, 1979.
Patent Abstracts of Japan, vol. 17 No. 124 (C-1035) JPA-4-3,004,882; Oct. 28, 1992.
Patent Abstracts of Japan, vol. 17 No. 391 (C-1087); Jul. 22, 1993 JPA-5-70,321; May 23, 1993.

*Primary Examiner*—Thurman K. Page
*Assistant Examiner*—P. Kulkosky
*Attorney, Agent, or Firm*—Jordan B. Bierman; Bierman and Muserlian

[57] ABSTRACT

The cosmetic composition of this invention which is a 2-methacryloyloxyethylphosphorylcholine polymer (Poly MPC) in a preferable amount of 0.001% to 10% by weight based on the total weight of the cosmetic composition. The cosmetic composition can repair damage to the skin and hair, such as dryness, loss of luster, etc. and enhance the moisture preservation capability thereof. It also has a good feel when applied.

5 Claims, 7 Drawing Sheets

$dw/da = \dfrac{\text{Water Phase}}{\text{Oil Phase}}$

● : The values when water phase is simply increased (Water/Lecithin) or when assumed that whole Poly-MPC presents in water phase (Water+Poly-MPC/ Lecithin)

○ : Actual values when Poly-MPC is added.

▲ : The values when whole Poly-MPC presents in Lecithin phase (Water/Lecithin+Poly-MPC)

FIG.7

COSMETIC COMPOSITION WITH CHOLINE DERIVATIVE

FIELD OF THE INVENTION

The present invention relates to a cosmetic composition and the agent, and more particularly, is directed to a cosmetic composition superior in preserving action of moisture in dry skin and protecting hair by the formation of a film thereon.

BACKGROUND OF THE INVENTION

Dryness of the skin is generally caused by a decrease in water content resulting from transepidemic water loss (hereinafter TEWL) which increases due to deterioration of the barrier function of the horny layers of the skin. This is caused by quantitative reduction of lipid secretion, particularly intercellular lipids and natural moisture factors such as amino acids. Therefore, dryness tends to increase in winter, with excessive skin washing, and the reduction of intercellular lipids and amino acids caused by age and state of health. In particular, when the water content in the horny layers has fallen to less than about 10%, the condition is called "dry skin". When skin is in the dried condition, skin gloss tend to decrease, and the appearance of fine wrinkles is observed.

Similarly, in a case of hair, harmful effects such as loss of hair smoothness and deterioration of luster tend to occur with reduction of hair water contents.

In the past, it was desired to prevent the lowering of the water content in the horny layers or hair and to maintain their normal functions. Therefore, various methods have been investigated to achieve such objectives. As a result, one method for inhibiting TEWL is by using occluding agents such as petroleum jelly ointment or emulsions in oil, which give good adhesion to skin and are hydrophobic. Another method for enhancing the hydration effect of cosmetic compositions is by combining a hygroscopic agent and/or a moisture preserving agent. Typically, these agents are selected from polysaccharides, such as hyaluronic acid and chitin; proteins, such as collagen and elastin; polyhydric alcohols, such as sorbitol, ethylene glycol, and glycerol; and organic acid salts, such as sodium pyrolidone carbonate and sodium lactate with a skin or hair treatment base. In addition, it has been found that ceramides and sphingolipids, which are components of the intercellular lipids in the horny layers and the like, play important roles in the preservation of water content, so that the combination of synthetic and/or naturally-extracted ceramides has been practically recommended.

However, the compositions according to the previously-known technique described above are not sufficiently effective in preserving moisture, and further, the use of the occluding agent gives an unpleasant oily or stick feel to the composition, while the hygroscopic agent and moisture preserving agent has a problem of must be used in high concentrations to assure sufficient efficacy in combination, thereby resulting in unpleasant oily and slimy feel. This makes it difficult to establish a suitable formulation which will provide the necessary high dose.

Furthermore, the cosmetic compositions provided according to the previously-known methods are less stable to periodic changes in absorbent conditions and are susceptible to attach by microorganisms.

On the other hand, a substance which can simultaneously provide (1) the hygroscopic and moisture preserving effects of hyaluronic acid and (2) the promotion and stabilization of the formation of the lamellar layer structure (comprising intercellular lipids) of ceramides, which can assist in the hygroscopic and moisture preserving function of the horny layers, has not yet been discovered.

It is an object of the present invention to provide a cosmetic composition which has a beautifying effect on skin and hair and is capable of reversing the damage due to drying such as rough skin, loss of hair luster, and also to provide moisture by preserving sufficient water content in the skin and hair as well as to have a pleasant feel when being applied.

The present inventors have found that the use of a copolymer of 2-methacryloyloxyethylphosphorylcholine and a hydrophobic monomer as components of a cosmetic composition can simultaneously preserve moisture on the skin and protect the hair; they have previously filed a patent application thereon (see Japanese OPI. Hei 5-70321). However, there is a need for a cosmetic composition which will provide still higher water retaining capacity.

SUMMARY OF THE INVENTION

The inventors have now found that a polymeric material comprising 2-methacryloyloxyethylphosphorylcholine as a constituent repeating unit and having the same structure as the polar group of phospholipid (phosphatidylcholine), which is a main component of biomembranes, has such a high moisture preserving effect, resulting from its hygroscopic and moisture properties, moreover it has excellent activity in promoting and stabilizing the lamella structure formation and in forming films.

Consequently, the present invention is directed to a cosmetic composition comprising the homopolymer of 2-methacryloyloxyethylphosphorylcholine; the present invention is also directed to a cosmetic composition comprising a polymer having a molecular weight of greater than 5,000, wherein the content of the polymer is 0.001 to 10% by weight based on the total weight of the cosmetic composition.

DETAILED DESCRIPTION OF THE INVENTION

Polymers of the present invention are obtained by polymerizing 2-methacryloyloxyethylphosphorylcholine (hereinafter MPC) of Formula I.

Formula I

To manufacture MPC, 2-bromoethylphosphoryl chloride, 2-hydroxyethylphosphoryl dichloride, and 2-hydroxyethylmethacrylate are reacted to produce 2-methacryloyloxyethyl-2'-bromoethyl phosphate, then 2-methacryloyloxyethyl-2'-bromoethyl phosphate is further reacted with trimethylamine in methanol solution to obtain MPC (A Collection of High Polymer Manuscripts, Vol. 35, 423–427, 1978). The process for manufacturing the polymer be carried out according to customary methods known in the arts by reacting MPC in a solvent and in the presence of a polymerization initiating agent.

The solvent to be used includes any solvent in which MPC is soluble; however, in practice, water, methanol, ethanol, propanol, t-butanol, benzene, toluene, dimethylformamide, tetrahydrofuran, chloroform and a mixture thereof are worthy of special mention. For the polymerization initiating agent, any radical initiating agent may be used; however, fatty acid azo compounds, such as 2,2'-azobisisobutylonitrile (AIBN), 3-carboxypropionitrile, and azobismalenonitrile; and organic peroxides, such as benzoyl peroxide, lauroyl peroxide, and potassium peroxide; are of particular value.

The examples for the synthesis of the polymer of this invention are described below.

Preparation 1. Synthesis of Poly(MPC)

MPC is dissolved in ethanol at a concentration of 0.5 mol/l, and 1 mol % of azobisisobutylonitrile (AIBN) based on the monomer is added thereto as an initiating agent. The solution is placed in a glass reactor under an inert atmosphere of argon gas, and is then sealed. The solution is reacted for 4 hours at 60° C., and a large amount of diethylether is then fed dropwise into the reacted mixture to precipitate the polymer. The precipitate is separated by filtration, washed thoroughly with di ethyl ether on a glass filter, and dried under vacuum. The yield is approximately 60%.

Preparation 2. Synthesis of Poly(MPC) having a terminal carboxy group

The reaction is carried out in the same manner as in Preparation 1 except azobis (3-carboxypropionitrile) is the initiating agent instead of AIBN. The reaction time is 3 hours, and the ratio of initiating agent to monomer is 3 mol % to adjust the molecular weight of the polymer which is obtained. The yield is approximately 30%.

Determination of IR ($cm^{-1}$)

3200-2900 ($CH_2$, $CH_3$), 1720 (C=O)
1100–1200 (C—O—C), 1250 (P=O)

Determination of molecular weight

According to the analysis of the polymer solution in water/ethanol (80/20 v/v) by gel permeation chromatography (hereinafter GPC), the molecular weight of the polymer was 37,000 determined as polyethyleneglycol.

The molecular weight of the polymer of this invention can be adjusted over a wide range; however, it is normally greater than 5,000, calculated as polyethyleneglycol (PEG), and is preferably greater than 10,000, considering feel, gelation, film formation, etc. Consequently, it is not preferable that the molecular weight of Poly MPC is lesser than the above values, because the moisture preserving function and the promotion and stabilization effects thereof on the lamella structure formation will accordingly decrease.

In the cosmetic composition of this invention, the polymer is normally present in an amount of 0.001 to 10% by weight, and preferably from 0.01 to 3% by weight, based on the total weight of the cosmetic composition. The cosmetic compositions of this invention can be used for skin treatment as toilet lotions, milky lotions, creams, lipsticks, foundations, etc. and for hair treatment as hair tonics, hair creams, hair lotions, and the like. In addition, by modifying the gelation and film-forming properties of the polymer, the cosmetic composition can also be used as massaging products and masks. Further, the cosmetic composition of this invention can be manufactured according to customary methods known in the art. Additionally, the cosmetic compositions of this invention can be combined with surface active agents, powders or pigments, antioxidants, ultraviolet absorbers, moisture preserving agents, vitamins, preservatives, perfumes, and the like.

The tests carried out for evaluating the hydroscopicity and stability of the polymers of this invention are described below.

Test 1. Hygroscopicity of MPC Polymer

Samples (A) MPC polymer (Molecular weight: 12,000)
(B) Chitosan (Reference material )

Method of Measurement

Figure 1:
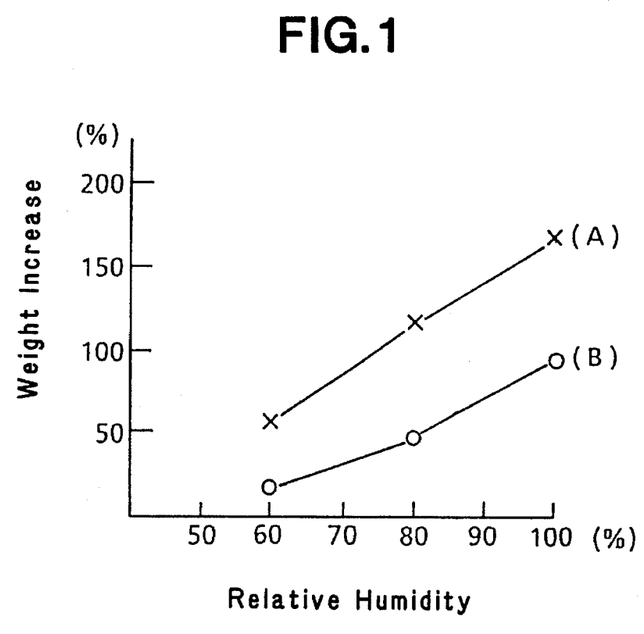
FIG. 1 is a diagram showing the correlation between relative humidity and percentage of water content.

5% by weight of MPC polymer in a 50% ethanol solution and 5% by weight of chitosan in an aqueous solution of acetic acid are prepared, and 5 ml of each of these solutions are spread over a 25 $cm^2$ teflon plate. The solvent in each solution is evaporated at room temperature to form a film of approximately 100 µm thickness. Samples of these films are separately placed in a desiccator at 20° C. for 48 hours and at relative humidities of 60%, 80%, and 95%, respectively, by using a saturated salt solution. The ratios of the weight increases were measured. The results are shown in FIG. 1. The ratio of weight increase (%)=[(Weight after 48 hours—Intial weight)/Initial weight]×100.

Results

As clearly seen from FIG. 1, the MPC polymer of this invention has higher hygroscopicity than that of chitosan, the reference material.

Test 2. Stability

Samples

MPC polymer (Molecular weight: 15,000)

Method of measurement

In four 10% aqueous solutions of ethanol, adjusted with various buffer solutions to the pH values of 4.0, 6.0, 8.0 and 9.0, respectively, the sample is dissolved at a concentration of 2% by weight. The solution is then allowed to stand for 3 months at 40° C., and the condition thereof is then examined. At the start of the tests, the solution appeared transparent and no coloring or precipitation was observed therein. The results are shown in Table 1.

TABLE 1

Stability of MPC Polymer in Solution

| Items Examined | pH 4.0 | pH 6.0 | pH 8.0 | pH 9.0 |
|---|---|---|---|---|
| Precipitation | None | None | None | None |
| Transparency | | Transparent | | |
| Coloring | None | None | None | None |

As shown in Table 1, the MPC polymer of this invention has excellent stability over a wide pH range.

Test 3. Hygroscopicity

Samples

1) Poly(MPC): 5% by weight solution in water
2) Poly(MPC$^{89}$-co-acrylate)(hereinafter MPC-AA): 5% by weight solution in water
3) PMPC-COOH: 5% by weight solution in water

Test Conditions

1) Humidity: R.H. 81% (NaCl) R.H. 41(CaCl$_2$.6H$_2$O)
2) Period for measurement: 1 to 3 days

Method of Measurement

5% by weight solution of each of test samples 1 to 3 in water is prepared and cast onto a polyethylene plate. The sample formed a membrane which is placed in a desiccator containing silica gel. A vacuum is applied by means of a vacuum pump, and the samples are allowed to stand for 9 days. Each sample is then measured to determine its dry weight. Thereafter, the hygroscopicity of each sample is measured by determining the change in weight after the sample was transferred into a desiccator maintained at the relative humidities set forth above.

Figure 5:
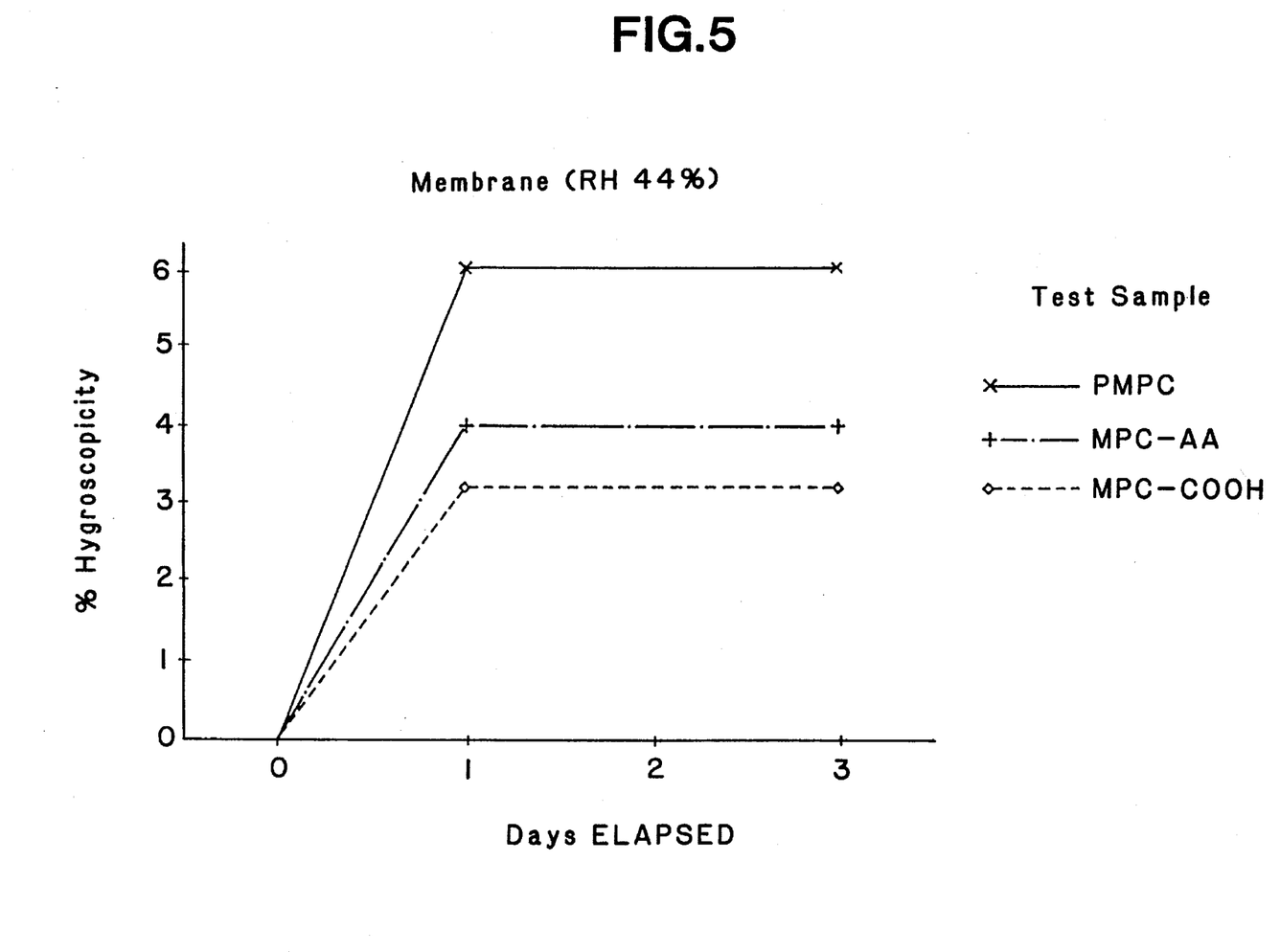
FIG. 5 is a diagram showing the results of the evaluation of hygroscopic properties of the samples at a relative humidity of 44%.
Figure 6:
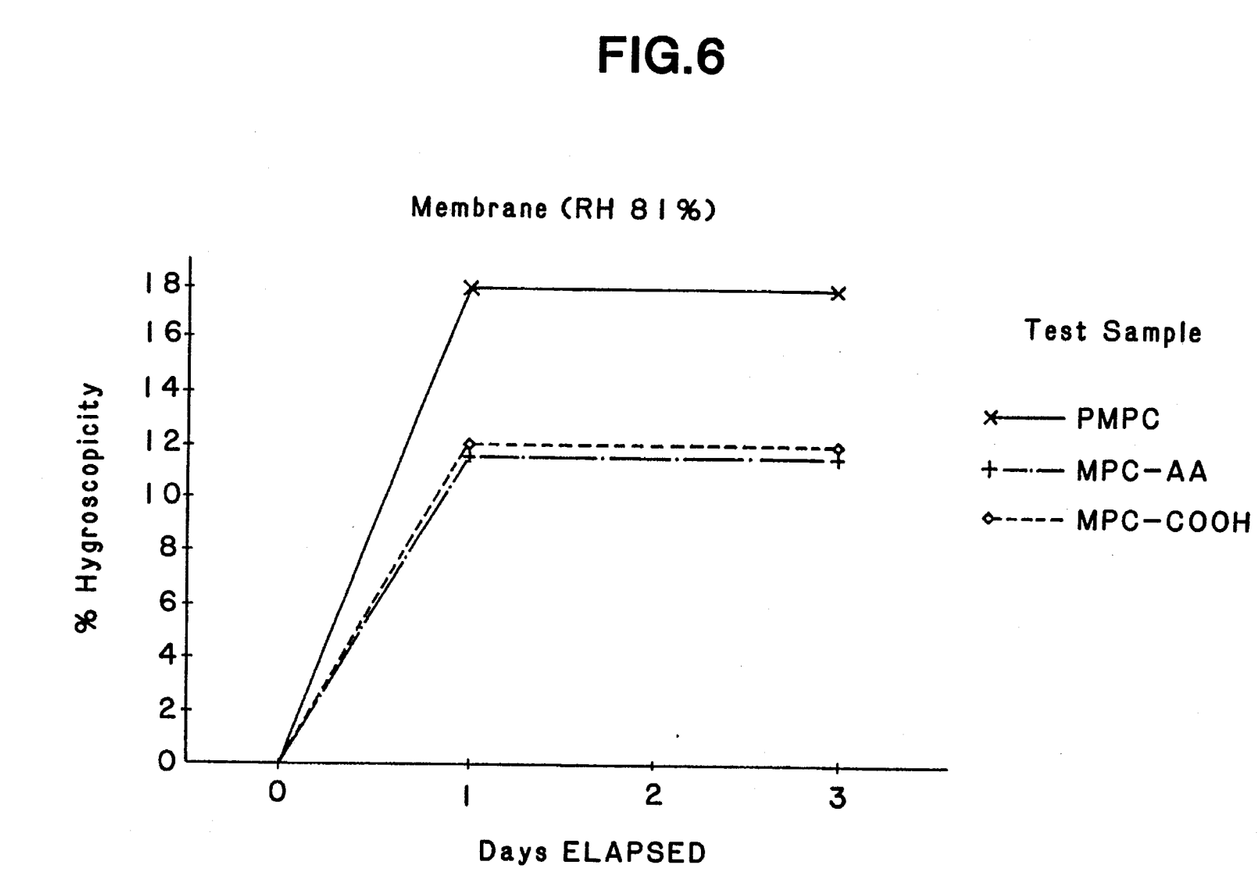
FIG. 6 is a diagram similar to that of FIG. 5 at a relative humidity of 81%.

As shown in FIGS. 5 and 6, Poly(MPC) showed higher hygroscopicity than that of MPC-AA or MPC-COOH at both relative humidities.

Test 4. Water holding capacity

Samples

1) Poly(MPC): 1% by weight in 5% by weight 1,3-butylenegylcol aqueous solution
   (A polymer of this invention; Formula I)
2) MPC-AA: 1% by weight in 5% by weight 1,3-butyleneglycol aqueous solution
   (Reference polymer; Formula II)
3) Hyaluronic acid (hereinafter HA): 1% by weight in 5% by weight 1,3-butyleneycol aqueous solution
   (Reference polymer; Formula III)

$$\left(\begin{array}{c}C\\|\\C-CH_2\\|\\C=O\\|\\O\\|\\CH_2CH_2OPOCH_2CH_2N^+(CH_3)_3\\|\\O^-\end{array}\right)_{89} - \left(\begin{array}{c}C-CH_2\\|\\COOH\end{array}\right)_{11} - \quad \text{Formula II}$$

$$HOOC-CH_2CH_2-\underset{\underset{C\equiv N}{|}}{\overset{\overset{CH_3}{|}}{C}}(CH_2-\underset{\underset{C=O}{|}}{\overset{\overset{CH_3}{|}}{C}})H \quad \text{Formula III}$$
$$\qquad\qquad\qquad\qquad\qquad O\\\qquad\qquad\qquad\qquad\qquad |\\\qquad\qquad\qquad\qquad\qquad CH_2CH_2OPOCH_2CH_2N^+(CH_3)_3\\\qquad\qquad\qquad\qquad\qquad |\\\qquad\qquad\qquad\qquad\qquad O^-$$

M.W. $7.1 \times 10^4$

Test Method

Figure 7:
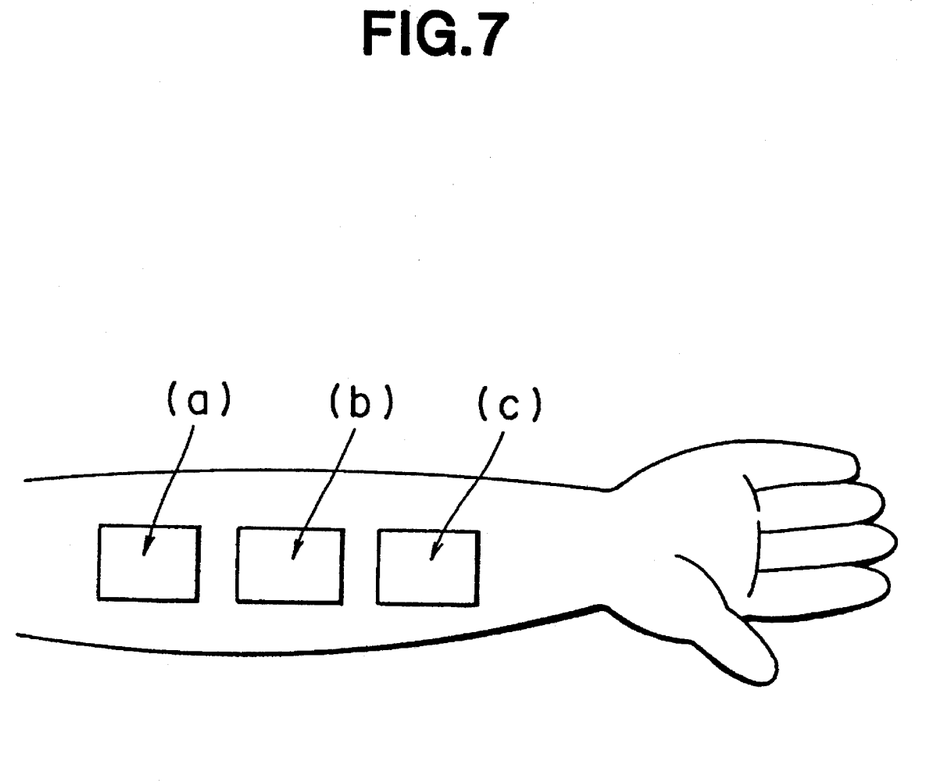
FIG. 7 is a diagram showing sites for measuring the water retaining capacity of the horny layer.

As illustrated in FIG. 7, three sites (each 3×3 cm) on the inside forearm were selected for the measurement.

Site (a): Measured prior to treatment, after application of 1% Poly(MPC), and after washing.

Site (b): Measured prior to treatment, after application of 1% MPC-AA, and after washing.

Site (c): Measured prior to treatment, after application of 1% HA, and after washing.

In Vivo Water Absorption-Desorption Test

Environment: R.H. 50%, 20° C.

Apparatus: Skin surface hydrometer (Type: Skicon 100, IBS Co.)

Procedure

① 1 droplet of distilled water was placed on the site, then wiped with dry gauze 10 seconds later.

② The conductance was measured immediately after wiping the droplet (0 second later), and 30, 60, 90, and 120 seconds later.

Flow chart of measurement procedure

Preparation of 3 sites on inside forearm
↓
Washing with soap
↓
Leaving for 20 minutes
↓

In vivo water absorption-desorption test

↓

Application of sample (1 sample/site, 22.6 μl/site)

↓

Leaving for 20 minutes

↓

In vivo water absorption-desorption test

↓

Washing with warm water

↓

Leaving for 20 minutes

↓

In vivo water absorption-desorption test

Water holding capacity (%)=(Average conductance value of 4 measurements during 30–120 sec. after water absorption)÷(Conductance value immediately (0 sec.) after water absorption)×100

Figure 8:
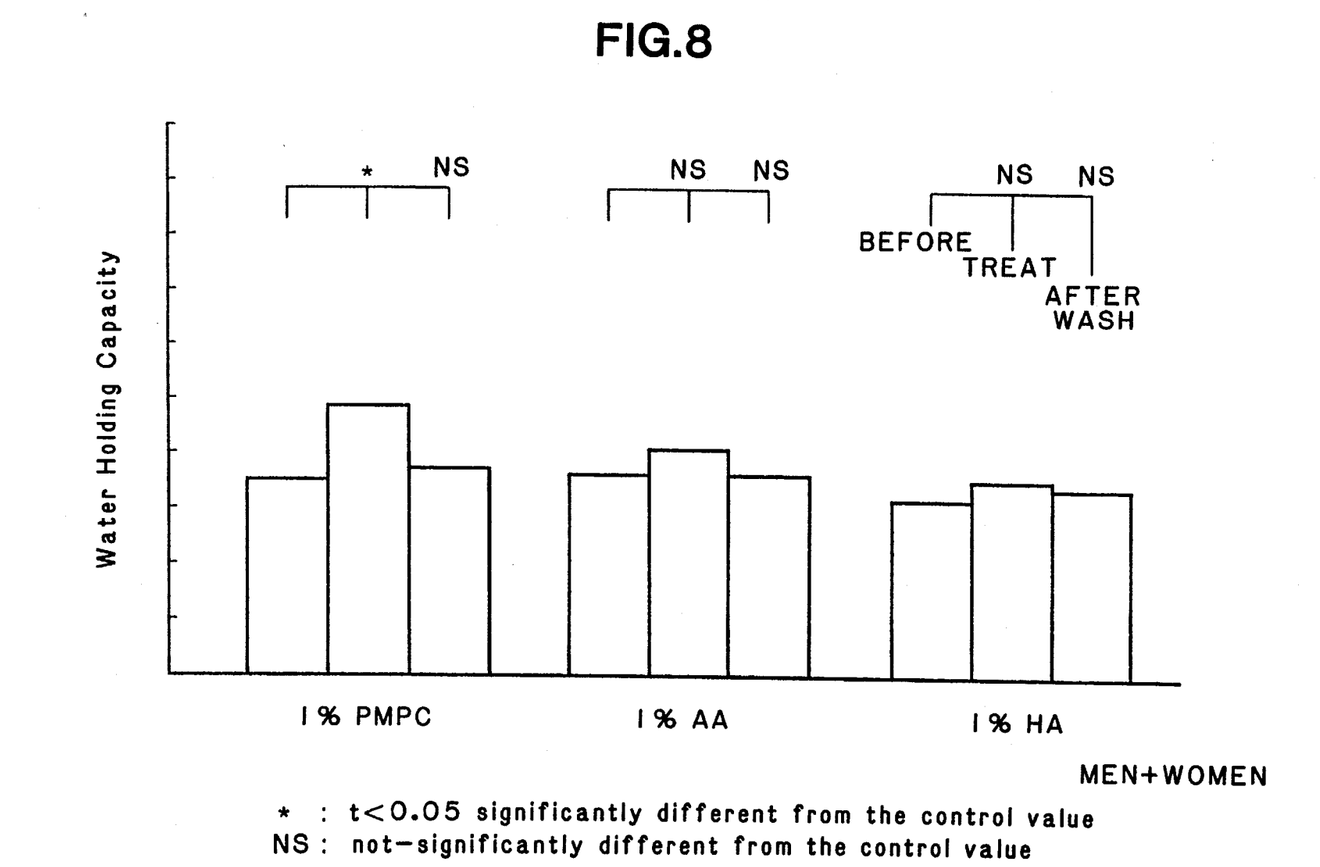
FIG. 8 is a diagram showing the results of the test on the water retaining capacity of the horny layer according to Paird-t-test method.

As can be seen from the results of the absorption-desorption test illustrated in FIG. 8, Poly(MPC) at a concentration of 1% shows water holding capacity after the application which is significantly improved over that prior to the application. Moreover, the effect is far greater than that obtained with HA and, while MPC-AA showed slight improvement, there was no significant improvement.

EXAMPLES

In the following Examples, which are illustrative only all amounts are in percent by weight.

| Example 1. o/w Type Milky Lotion | |
|---|---|
| Stearic acid | 1 |
| Beeswax | 2 |
| Microcrystalline wax | 1 |
| 3% MPC polymer aqueous solution (Molecular weight: 100,000) | 30 |
| Propyleneglycol | 5 |
| Glycerin | 2 |
| Ethanol | 5 |
| Preservative | 0.3 |
| Perfume | 0.3 |
| Water | 53.4 |
| Example 2. Toilet Lotion | |
| MPC polymer 2% aqueous solution (Molecular weight: 20,000) | 25 |
| Glycerin | 1.5 |
| Ethanol | 6 |
| Propyleneglycol | 1.5 |
| Citric acid | 0.01 |
| Sodium citrate | 0.1 |
| Perfume | 0.05 |
| Water | 65.84 |
| Example 3. Cream | |
| Squalane | 5 |
| 2-ethylhexanoate triglyceride | 1 |
| Petroleum jelly | 0.5 |
| 3% MPC polymer aqueous solution (Molecular weight: 20,000) | 50 |
| Glycerin | 3 |
| 1,3-butanediol | 4 |
| Polyglycerinpolyoxybutylenestearylether | 2.5 |
| Perfume | 0.2 |
| Water | 33.8 |
| Example 4. Hair Lotion | |
| MPC polymer 2% aqueous solution (Molecular weight: 45,000) | 5 |
| Ethanol | 10 |
| Glycerin | 3 |
| Carboxymethyl chitin | 0.01 |
| Vitamin E | 0.1 |
| Coloring matter | 0.02 |
| Water | 81.87 |
| Example 5. Hair Cream | |
| Squalane | 30.0 |
| Petroleum jelly | 3.0 |
| Beeswax | 4.0 |
| Stearic acid | 4.0 |
| Olive oil | 2.0 |
| Sorbitanmonostearate | 2.5 |
| Polyoxyethylenesorbitanmonostearate | 2.5 |
| Butylparaben | 0.1 |
| 10% MPC polymer aqueous solution (Molecular weight: 60,000) | 30 |
| 1,3-butanediol | 2.5 |
| Polyethyleneglycol 200 | 1.5 |
| Triethanolamine | 1.0 |
| Methylparaben | 0.1 |
| Perfume | 0.2 |
| Water | 16.6 |

Comparative Test

The cosmetic composition according to this invention is compared with conventional cosmetics as to improvement of dry skin and hair protection.

Test 3. Improving Effect on Dry Skin Induced by sodium dodecylsulfate (SDS) Solution Samples (A) The milky lotion of Example 1 of this invention.

(B) A conventional milky lotion which is the same as the milky lotion of Example 1 except that purified water is substituted for the MPC polymer.

Test Method

The beneficial effect of the composition on artificial dry skin formed by applying a surface active agent is examined based on the determination of water content in the horny layers and the assessment of efflorescence of ten Japanese females from 20 to 37 years of age. For this evaluation, rough dry skin is engendered by treating the skin with 10 ml of 5% SDS in a glass cup 3 cm in diameter, the cup is tightly fitted to the skin inside of the forearm, and is allowed to remain for 10 min. with slight shaking; the solution is then recovered. The treatment was repeated at the same site with the same quantity of the same solution; however, this time the cup is kept on the skin for 20 min., and the solution is then recovered. Starting one day after the foregoing treatment with SDS, a sample of milky lotion (A) or (B) is applied to the treated site twice daily. The water content in the horny layers before and after the tests are determined by measurement of the skin surface conductance according to the method described below. The results in mean values of efflorescence assessed according to the criteria described below are shown in Tables 2 and 3, respectively.

1) Water content in the horny layers

The water content in the horny layers is determined by using a capacitance conductance meter (IBM, Model IB-354) according to the method of Tagami et al. (see "In vivo analysis on water holding capacity in the horny layer of skin", Japanese Journal of Dormatology, 92(13), 1363–1367, 1982). The site to be measured is washed with warm water at 37° C. for 30 seconds, and followed by five measurements at 20° C. and relative humidity of 50% to obtain the mean values.

2) Criteria for the assessment of efflorescence

0: No changes of dry skin are seen.
1: Slight changes of dry skin are seen.
2: Clear changes of dry skin are seen.
3: Severe changes of dry skin are seen.

Figure 2:
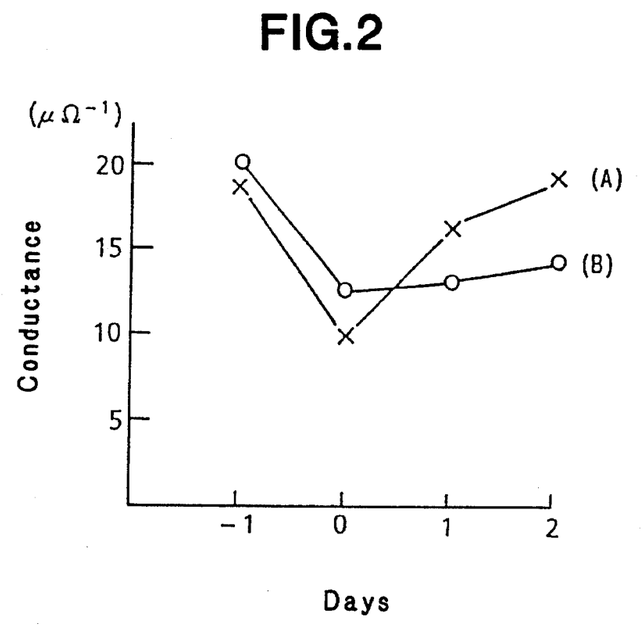
FIG. 2 is a diagram showing the correlation between time and the conductance of the skin (which indicates water content)
Figure 3:
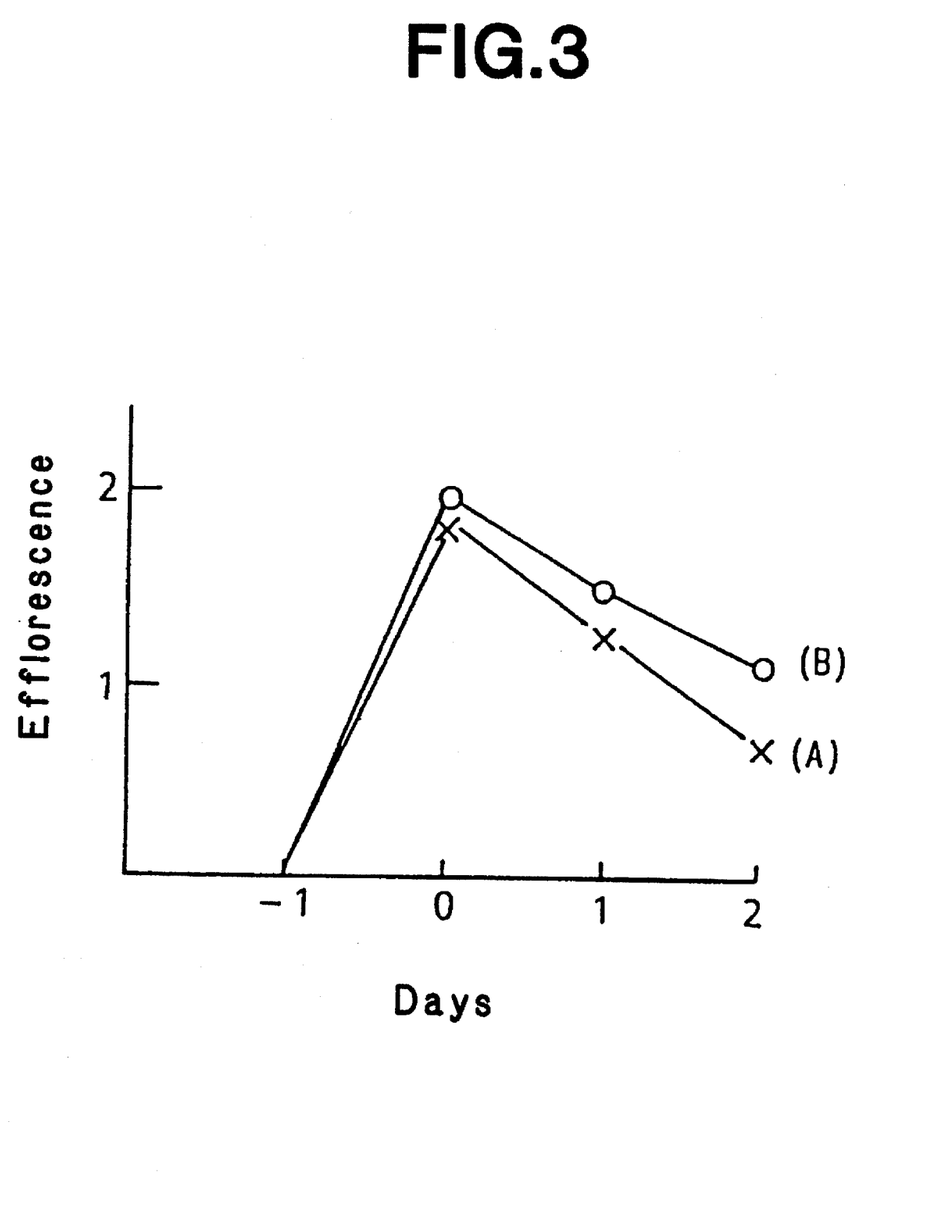
FIG. 3 is a diagram showing the correlation between time and efflorescence.

As shown in FIGS. 2 and 3, sample (A), the milky lotion of this invention, has an outstanding effect on the recovery of water content in the horny layers, this is shown by the conductance at the skin surface, and atrophic efflorescence in comparison with sample (B), the conventional milky lotion.

Test 4. Practical Use Tests

Samples

The samples are sample (A) and (B) used in the Test 3.

Test Method

40 Japanese females from 20 to 49 years of age, who have dry skin or atrophic symptoms every day are divided at random into A and B groups (20 each). The milky lotion of sample (A) is used by those in group A for one month, while the milky lotion of sample (B) is used by those in group B for the same period. The beautifying effect on the skin, such as moisture feel which depends on moisture retention and improvement in suppleness of the skin (which depends on skin activation), after one month and the feel at the time of use, (e.g. sticky feel) are compared. The results are shown in Table 2.

TABLE 2

| | Practical Use Tests | | |
| --- | --- | --- | --- |
| | Beautifying Effect | | Feeling |
| | Moist | Supple | Sticky |
| A Group | 18/20 | 13/20 | 1/20 |
| B Group | 5/20 | 2/20 | 0/20 |

As clearly seen from the results in Table 2, sample (A), the lotion of the invention, has no more problem in feel than does sample (B), the conventional milky lotion. However, the wanted lotion provided of superior beautifying effect on the skin, including moisture preservation and skin activation compared to the conventional lotion.

Test 5. Hair Protecting Effect

Samples (C) Hair lotion of Example 4 of this invention.
(D) A conventional hair lotion which is the same as the lotion of Example 4 except that purified water is substituted for the MPC polymer.

Test Method

A predetermined amount of the hair lotions of samples (C) or (D) is applied to a 10 g bundle of hairs (10 cm in length) collected from Japanese females, which hairs have not been permanent waved or bleached. After application of the sample, the hairs are air-dried. The assessment based on physical functions is made by five panelists according to the criteria indicated in Table 3 shown below, and the averages of the points awarded are set forth in Table 4. These assessments are conducted with respect to hair smoothness, hair luster, and hair moisture feel, which depend upon the ability to retain moisture.

TABLE 3

Criteria for Assessment based on Physical Functions

Smoothness: Inferior |—|—|—|—|—| Excellent
              0  1  2  3  4  5

Luster: None |—|—|—|—|—| Clear
              0  1  2  3  4  5

Moisture feeling: None |—|—|—|—|—| Clear
              0  1  2  3  4  5

TABLE 4

Results of Assessment based on Physical Functions In Mean Values

| | Smoothness | Luster | Moisture Feel |
| --- | --- | --- | --- |
| Sample (C) | 4.6 | 3.6 | 4.6 |
| Sample (D) | 2.9 | 2.6 | 2.9 |

As shown in Table 4, it is clear that sample (C), the present invention, is superior in all of the characteristics tested, namely smoothness, luster, and moisture feel in comparison with sample (D), the conventional lotion.

Test 6. Stabilization of Lamellar Layer Structure

Lamellae were prepared with lecithin (Egg Phosphatidyl Cholin; EPC) of an intercellular lipid-like substance. The object is to determine whether the MPC polymer can regularize the lamellar structure comprising lecithin and also to reduce the interval between the molecules, i.e. to stabilize and promote the formation of lamellar layers. The determination is carried out by using X-rays with small angle scattering.

Test Method

Figure 4:
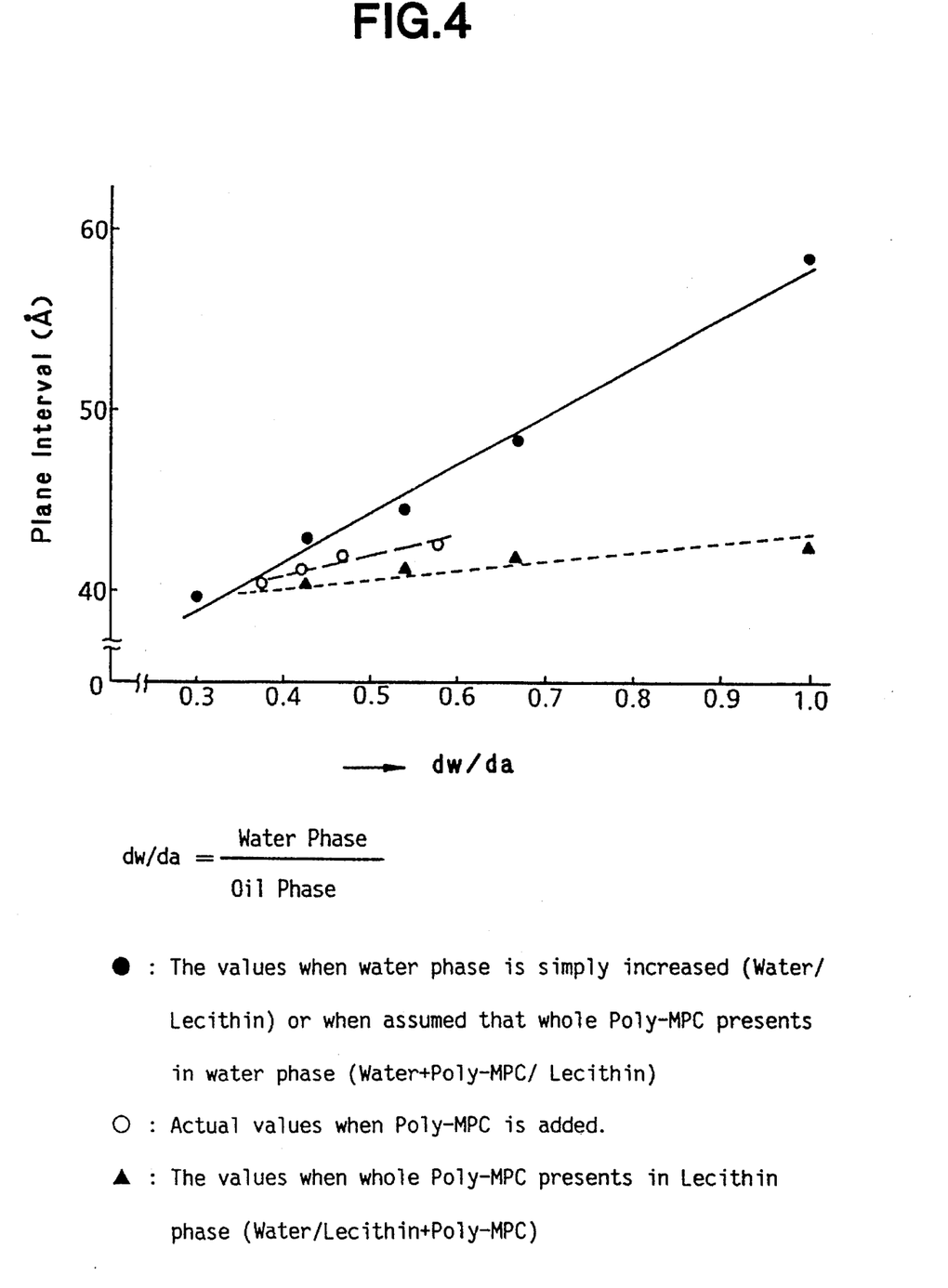
FIG. 4 is a diagram showing the correlation between the water phase/oil phase ratio and the distance between lamellar layers.

Lecithin and water are combined in the weight ratio of 90:10 to 65:35 to prepare the reference lamella phases. Also, test lamella phases are prepared by replacing a part of the water in the control phases with the MPC polymer, and then mixing. The plane intervals between the phases obtained are measured by an X-ray diffractometer (Model: JDX-3500; Manufactured by Nippon Densi). The results are shown in FIG. 4.

Conditions for Measurement

Small-angle scattering apparatus:
Model: DX-LSV3, Manufactured by Nippon Densi
Detector: Scintillation counter
Source of ray: Cu-ray
Voltage: 45 KV
Current: 200 mA
Temperature at measuring: 22–24° C.

The samples were measured by putting them between 4 μm layers of mylar and placed in a cell holder.

Results

As shown in FIG. 4, the mixture of lecithin and water combines in the weight ratio of 90:10 to 65:35 to form lamella phases having a layered structure with plane intervals of 39 to 58Å. As the water in the mixture was replaced with the MPC polymer solution, the d value, which is described below, was lowered accordingly. Further, it was found, from the small-angle scattering peaks (not shown), that the pattern of direction and the arrangement of the molecules of lecithin were better regulated in the MPC polymer composition than in the comparative composition.

Since the plane interval d between the lamella liquid crystal phases comprises a hydrophobic part (lecithin layer) da and a water layer part dw, it is considered that the lowering of d by replacing the water with the MPC polymer indicates that the MPC polymer enters into the lecithin layer; also, it is considered that the arrangement and the regularity of lecithin molecules are improved because of this.

For these reasons, the foregoing demonstrates that the MPC polymer prevents dry skin due to its hygroscopicity and stabilizing effect on the lamellar layers having lipids which are located between the human horny layers.

The cosmetic composition according to this invention is far superior in moisture retention, promotion and stabilizing action of lamella formation, beautifying effect on the skin resulting from film formation, etc. It also has a beautifying effect on hair, and can be used without problems in term of safety.

What we claim is:

1. A cosmetic composition comprising 0.001% to 10% by weight of a homopolymer of 2-methacryloyloxyethylphosphorylcholine and a cosmetically acceptable carrier, said homopolymer having a molecular weight greater than 5,000.

2. The composition of claim 1 wherein said molecular weight is at least 10,000.

3. The composition of claim 1 wherein said molecular weight does not exceed 100,000.

4. A method of preserving moisture in human skin comprising applying a homopolymer of 2-methacryloyloxyethylphosphorylcholine to the skin.

5. A method of preserving moisture in human hair comprising applying a homopolymer of 2-methacryloyloxyethylphosphorylcholine to the hair.

* * * * *